United States Patent
Müller et al.

[11] Patent Number: 6,156,760
[45] Date of Patent: Dec. 5, 2000

[54] FUNGICIDE MIXTURES

[75] Inventors: Ruth Müller, Friedelsheim; Herbert Bayer; Hubert Sauter, both of Mannheim; Eberhard Ammermann, Heppenheim; Gisela Lorenz, Hambach; Siegfried Strathmann, Limburgerhof; Klaus Schelberger, Gönnheim; Maria Scherer, Landau; Joachim Leyendecker, Ladenburg; Bernd Müller, Frankenthal, all of Germany

[73] Assignee: BASF Aktiengesellschaft, Ludwigshafen, Germany

[21] Appl. No.: 09/155,110

[22] PCT Filed: Apr. 22, 1997

[86] PCT No.: PCT/EP97/02023

§ 371 Date: Sep. 21, 1998

§ 102(e) Date: Sep. 21, 1998

[87] PCT Pub. No.: WO97/40685

PCT Pub. Date: Nov. 6, 1997

[30] Foreign Application Priority Data

Apr. 26, 1996 [DE] Germany ............... 196 16 720
Apr. 29, 1996 [DE] Germany ............... 196 17 070
Sep. 2, 1996 [DE] Germany ............... 196 35 506

[51] Int. Cl.[7] .................. A01N 43/54; A01N 43/56; A01N 43/64; A01N 37/18; A01N 37/52
[52] U.S. Cl. .................. 514/275; 514/383; 514/407; 514/508; 514/538; 514/618; 514/619
[58] Field of Search .................. 514/383, 407, 514/275, 508, 538, 618, 619

[56] References Cited

U.S. PATENT DOCUMENTS

| | | | |
|---|---|---|---|
| 4,814,338 | 3/1989 | Ito et al. ............. | 514/275 |
| 4,931,560 | 6/1990 | Hubele ............. | 544/315 |
| 5,508,283 | 4/1996 | Eicken et al. ............. | 514/275 |
| 5,589,479 | 12/1996 | Eicken et al. ............. | 514/275 |
| 5,591,747 | 1/1997 | Eicken et al. ............. | 514/275 |

FOREIGN PATENT DOCUMENTS

| | | |
|---|---|---|
| 2 279 568 | 1/1995 | United Kingdom . |
| 9601256 | 1/1996 | WIPO . |
| 9601258 | 1/1996 | WIPO . |

OTHER PUBLICATIONS

Pesticide Sci., Bd. 44, N4. 1, May 1995, 77–79.

*Primary Examiner*—Allen J. Robinson
*Attorney, Agent, or Firm*—Keil & Weinkauf

[57] ABSTRACT

Fungicidal mixtures, comprising
  a) an oxime ether of the formula I

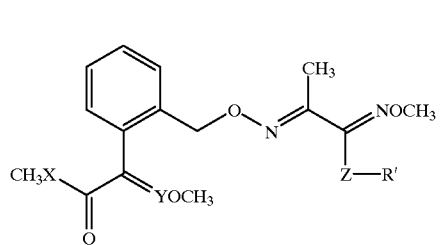

where the substituents have the following meanings:

X is oxygen or amino (NH);

Y is CH or N;

Z is oxygen, sulfur, amino (NH) or $C_1$–$C_4$-alkylamino (N—$C_1$–$C_4$-alkyl);

R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-Cycloalkylmethyl, or is benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio and/or b) a carbamate of the formula II

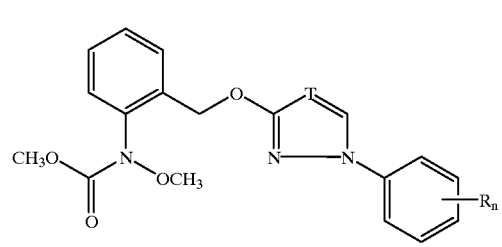

where T is CH or N, n is 0, 1 or 2 and R is halogen, $C_1$–$C_4$-alkyl or $C_1$–$C_4$-haloalkyl, it being possible for the radicals R to be different when n is 2, and c) a pyrimidine derivative of the formula III

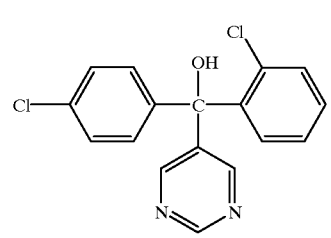

where R is methyl, propyn-1-yl or cyclopropyl, in a synergistically active amount.

23 Claims, No Drawings

FUNGICIDE MIXTURES

This application is a 371 of PCT/EP97/02023, filed Apr. 22, 1997.

The present invention relates to a fungicidal mixture which comprises a) an oxime ether of the formula I

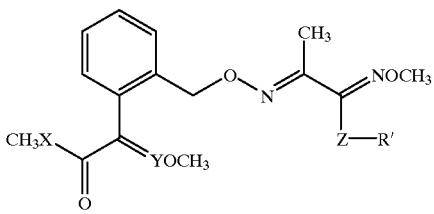

where the substituents have the following meanings:

X is oxygen or amino (NH);
Y is CH or N;
Z is oxygen, sulfur, amino (NH) or $C_1$–$C_4$-alkylamino (N—$C_1$–$C_4$-alkyl);
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or can have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio and/or b) a carbamate of the formula II

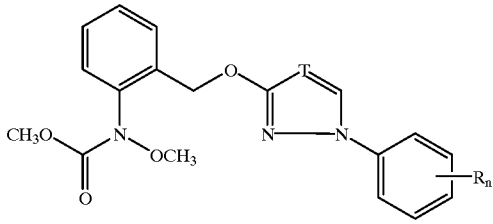

where T is CH or N, n is 0, 1 or 2 and R is halogen, $C_1$–$C_4$-alkyl or $C_1$–$C_4$-haloalkyl, it being possible for the radicals R to be different when n is 2, and c) a pyrimidine derivative of the formula III

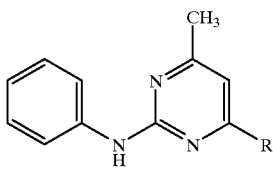

where R is methyl, propyn-1-yl or cyclopropyl, in a synergistically active amount.

Moreover, the invention relates to methods of controlling harmful fungi with the compounds I and/or II and III or synergistic mixtures comprising them, and to the use of the compounds I and/or II and the compounds III, respectively, for the preparation of such mixtures.

The compounds of the formula I, their preparation and their action against harmful fungi have been disclosed in the literature (WO-A 95/21,153, WO-A 95/21,154, DE-A 195 28 651.0).

Compounds of the formula II, their preparation and their action against harmful fungi have been described in WO-A 96/01,256 and WO-A 01,258.

The pyrimidine derivatives III, their preparation and their action against harmful fungi have also been disclosed [R=methyl: DD-A 151 404 (common name: pyrimethanil); R=1-propynyl: EP-A 224 339 (common name: mepanipyrim); R=cyclopropyl: EP-A 310 550].

It was an object of the present invention to provide mixtures which have an improved activity gainst harmful fungi combined with a reduced total amount of active ingredients applied (synergistic mixtures) with a view to reducing the rates of application and to improving the spectrum of action of the known compounds.

Accordingly, we have found that this object is achieved by the mixture defined at the outset. Moreover, we have found that better control of the harmful fungi is possible by applying the compounds I and/or II and the compounds III simultaneously together or separately or by applying the compounds I and/or II and the compounds III in succession than when just the compounds I and/or II or III are used.

In particular, the general formula I represents oxime ethers in which X is oxygen and Y is CH or X is amino and Y is N.

Moreover, preferred compounds I are those where Z is oxygen.

Equally, preferred compounds I are those where R' is alkyl or benzyl.

Especially preferred with a view to their use in the synergistic mixtures according to the invention are the compounds I compiled in the tables which follow:

Table 1.

Compounds of the formula IA where ZR' for each compound corresponds to one line of Table A

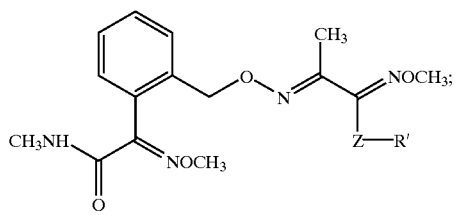

Table 2.

Compounds of the formula IB where ZR' for each compound corresponds to one line of Table A

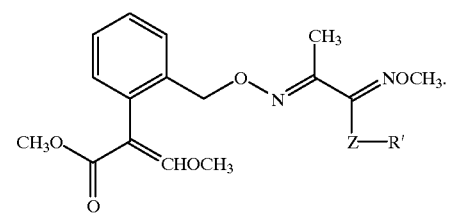

TABLE A

| No. | ZR' |
|---|---|
| I.1 | O—$CH_2CH_2CH_3$ |
| I.2 | O—$CH(CH_3)_2$ |
| I.3 | O—$CH_2CH_2CH_2CH_3$ |
| I.4 | O—$CH(CH_3)CH_2CH_3$ |

TABLE A-continued

| No. | ZR' |
|---|---|
| I.5 | O—CH$_2$CH(CH$_3$)$_2$ |
| I.6 | O—C(CH$_3$)$_3$ |
| I.7 | S—C(CH$_3$)$_3$ |
| I.8 | O—CH(CH$_3$)CH$_2$CH$_2$CH$_3$ |
| I.9 | O—CH$_2$C(CH$_3$)$_3$ |
| I.10 | O—CH$_2$C(Cl)=CCl$_2$ |
| I.11 | O—CH$_2$CH=CH—Cl (trans) |
| I.12 | O—CH$_2$C(CH$_3$)=CH$_2$ |
| I.13 | O—CH$_2$-(cyclopropyl) |
| I.14 | O—CH$_2$—C$_6$H$_5$ |
| I.15 | O—CH$_2$—[4-F—C$_6$H$_4$] |
| I.16 | O—CH$_2$CH$_3$ |
| I.17 | O—CH(CH$_2$CH$_3$)$_2$ |

In relation to the C=Y double bond, the compounds of the formula I can be in the E or the Z configuration (in relation to the carboxylic acid function). Accordingly, they can be used in the mixture according to the invention in each case either in the form of pure isomers or else in the form of an E/Z isomer mixture. The E/Z isomer mixture or the E isomer are preferably used in each case, the E isomer being especially preferred in many cases.

The C=N double bonds of the oxime ether groups in the side chain of the compounds I can be in each case in the form of pure E or Z isomers or in the form of E/Z isomer mixtures. The compounds I can be used in the mixtures according to the invention as isomer mixtures or else as pure isomers. With a view to their use, compounds I which are particularly preferred are those where the terminal oxime ether group of the side chain is in the cis configuration (OCH$_3$ group relative to ZR').

In particular, the formula II represents carbamates where the combination of the substituents corresponds to one line of the table which follows:

TABLE 3

| No. | T | R$_n$ |
|---|---|---|
| II.1 | N | 2-F |
| II.2 | N | 3-F |
| II.3 | N | 4-F |
| II.4 | N | 2-Cl |
| II.5 | N | 3-Cl |
| II.6 | N | 4-Cl |
| II.7 | N | 2-Br |
| II.8 | N | 3-Br |
| II.9 | N | 4-Br |
| II.10 | N | 2-CH$_3$ |
| II.11 | N | 3-CH$_3$ |
| II.12 | N | 4-CH$_3$ |
| II.13 | N | 2-CH$_2$CH$_3$ |
| II.14 | N | 3-CH$_2$CH$_3$ |
| II.15 | N | 4-CH$_2$CH$_3$ |
| II.16 | N | 2-CH(CH$_3$)$_2$ |
| II.17 | N | 3-CH(CH$_3$)$_2$ |
| II.18 | N | 4-CH(CH$_3$)$_2$ |
| II.19 | N | 2-CF$_3$ |
| II.20 | N | 3-CF$_3$ |
| II.21 | N | 4-CF$_3$ |
| II.22 | N | 2,4-F$_2$ |
| II.23 | N | 2,4-Cl$_2$ |
| II.24 | N | 3,4-Cl$_2$ |
| II.25 | N | 2-Cl, 4-CH$_3$ |
| II.26 | N | 3-Cl, 4-CH$_3$ |
| II.27 | CH | 2-F |
| II.28 | CH | 3-F |
| II.29 | CH | 4-F |
| II.30 | CH | 2-Cl |
| II.31 | CH | 3-Cl |
| II.32 | CH | 4-Cl |
| II.33 | CH | 2-Br |
| II.34 | CH | 3-Br |
| II.35 | CH | 4-Br |
| II.36 | CH | 2-CH$_3$ |
| II.37 | CH | 3-CH$_3$ |
| II.38 | CH | 4-CH$_3$ |
| II.39 | CH | 2-CH$_2$CH$_3$ |
| II.40 | CH | 3-CH$_2$CH$_3$ |
| II.41 | CH | 4-CH$_2$CH$_3$ |
| II.42 | CH | 2-CH(CH$_3$)$_2$ |
| II.43 | CH | 3-CH(CH$_3$)$_2$ |
| II.44 | CH | 4-CH(CH$_3$)$_2$ |
| II.45 | CH | 2-CF$_3$ |
| II.46 | CH | 3-CF$_3$ |
| II.47 | CH | 4-CF$_3$ |
| II.48 | CH | 2,4-F$_2$ |
| II.49 | CH | 2,4-Cl$_2$ |
| II.50 | CH | 3,4-Cl$_2$ |
| II.51 | CH | 2-Cl, 4-CH$_3$ |
| II.52 | CH | 3-Cl, 4-CH$_3$ |

The compounds II.12, II.23; II.32 and II.38 are especially preferred.

Due to the basic character, the compounds of the formulae I to III are capable of forming salts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, carboxylic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphonic acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can in this case be in the various valences which they can assume.

When preparing the mixtures, it is preferred to employ the pure active ingredients, with which further active ingredients against harmful fungi or other pests such as insects, arachnids or nematodes, or else herbicidal or growth-regulating active ingredients or fertilizers can be admixed, if so desired.

The mixtures of the compounds I and/or II and III, or the simultaneous joint or separate use of the compounds I and/or II and III, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants such as cotton, vegetable species (eg. cucumbers, beans and curcubits), barley, grass, oats, coffee, maize, fruit species, rice, rye, soybeans, grapevine, wheat, ornamentals, sugar cane, and a variety of seeds.

They are particularly suitable for controlling the following phytopathogenic fungi: *Erysiphe graminis* (powdery mildew) on cereals, *Erysiphe cichoracearum* and *Sphaerotheca fuliginea* on curcubits, *Podosphaera leucotricha* on apples, *Uncinula necator* on grapevines, Puccinia species on cereals, Rhizoctonia species on cotton, rice and lawn, Ustilago species on cereals and sugar cane, *Venturia inaequalis* (scab) on apples, Helminthosporium species on cereals, *Rhynchosporium secalis, Septoria nodorum* on wheat, *Botrytis cinerea* (gray mold) on strawberries, vegetables, ornamentals and grapevines, *Cercospora arachidicola* on peanuts, *Pseudocercosporella herpotrichoides* on wheat and barley, *Pyricularia oryzae* on rice, *Phytophthora infestans* on potatoes and tomatoes, *Plasmopara viticola* on grapevines, Alternaria species on vegetables and fruit, and Fusarium and Verticillium species.

Furthermore, they can be used in the protection of materials (eg. in the protection of wood), for example against *Paecilomyces variotii*.

The compounds I and/or II and III can be applied simultaneously together or separately or in succession, the sequence, in the case of separate application, generally not having any effect on the result of the control measures.

The compounds I and/or II and III are normally used in a weight ratio of from 20:1 to 0.1:2, preferably 10:1 to 0.1:1, in particular 5:1 to 0.2:1.

The application rates of the mixtures according to the invention are from 0.01 to 3 kg/ha, preferably 0.1 to 1.5 kg/ha, in particular 0.4 to 1.0 kg/ha, depending on the nature of the desired effect.

In the case of the compounds I and/or II, the application rates are in general from 0.01 to 0.5 kg/ha, preferably 0.05 to 0.5 kg/ha, in particular 0.05 to 0.2 kg/ha.

Correspondingly, in the case of the compounds III, the application rates are normally from 0.1 to 1.0 kg/ha, preferably 0.4 to 1.0 kg/ha, in particular 0.4 to 0.8 kg/ha.

For seed treatment, the application rates of the mixture are generally from 0.001 to 50 g/kg seed, preferably 0.01 to 10 g/kg, in particular 0.01 to 8 g/kg.

If phytopathogenic harmful fungi are to be controlled, the separate or joint application of the compounds I and II or of the mixtures of the compounds I and/or II and III is effected by spraying or dusting the seeds, the plants or the soils before or after sowing of the plants, or before or after plant emergence.

The fungicidal synergistic mixtures according to the invention, or the compounds I and/or II and III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl polyglycol ethers or tributylphenyl polyglycol ether, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, ligninsulfite waste liquors or methylcellulose.

Powders, materials for spreading and dusts can be prepared by mixing or jointly grinding the compounds I and/or II and III or the mixture of the compounds I and/or II and III with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I and/or II or III, or of the mixture of the compounds I and/or II and III. The active ingredients are employed in a purity of from 90% to 100%, preferably 95% to 100% (according to NMR spectrum or HPLC).

The compounds I and/or II or III, or the mixtures, or the corresponding formulations, are applied by treating the harmful fungi or the plants, seeds, soils, areas, materials or spaces to be kept free from them with a fungicidally active amount of the mixture, or of the compounds I and/or II and III in the case of separate application. Application can be effected before or after infection by the harmful fungi.

The fungicidal activity of the compounds and of the mixtures was demonstrated by the following experiments:

The active ingredients, separately or together, are formulated as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

Evaluation is carried out by determining the infected leaf areas in percent. These percentages are converted into efficacies. The expected efficacies of the mixtures of the active ingredients are determined using Colby's formula [R. S. Colby, Weeds 15, 20–22 (1967)] and compared with the observed efficacies.

Colby's formula:

$$E = x+y-x \cdot y/100$$

E expected efficacy, expressed in % of the untreated control, when using the mixture of the active ingredients A and B at concentrations of a and b x efficacy, expressed in % of the untreated control, when using active ingredient A at a concentration of a y efficacy, expressed in % of the untreated control, when using active ingredient B at a concentration of b The efficacy (W) is calculated as follows using Abbot's formula:

$$W = (1-\alpha) \cdot 100/\beta$$

α is the fungal infection of the treated plants in % and

β is the fungal infection of the untreated (control) plants in %

An efficacy of 0 means that the infection level of the treated plants corresponds to that of the untreated control plants; an efficacy of 100 means that the treated plants are not infected.

EXAMPLES 1–17

Protective Activity Against *Puccinia recondita* on Wheat (Leaf Rust on Wheat)

Leaves of wheat seedlings cv. "Frühgold" in pots were sprayed to run-off with an aqueous spray mixture which had been prepared with a stock solution of 10% active ingredient, 63% cyclohexanone and 27% emulsifier. The next day, the leaves were moistened and dusted with leaf rust spores (*Puccinia recondita*). The pots were subsequently placed for 24 hours into a chamber with high atmospheric humidity (90 to 95%) at from 20 to 22° C. During this time, the spores germinated, and the germination tubes penetrated the plant tissue for a further 7 days at from 20 to 22° C. and a relative atmospheric humidity of from 65 to 70%. The extent of rust development on the leaves was then determined visually.

The visually determined values for the percentage of infected leaf area were transformed into efficacy in percent of the untreated control. An efficacy of 0 is the same infection level as in the untreated control, an efficacy of 100 is an infection level of 0%. The expected efficacies for combinations of active ingredients were calculated using Colby's formula (Colby, S. R. (Calculating synergistic and antagonistic responses of herbicide Combinations", Weeds, 15, p. 20–22, 1967) and compared with the observed efficacies.

TABLE 4

|  | Active ingredient or combination | Active ingredient concentration in the spray mixture in ppm | Efficacy in % of the untreated control |
|---|---|---|---|
| 1V | Control (untreated) | (Infection level 100%) | 0 |
| 2V | Table 1 A No. 2 = A | 12.5 | 40 |
|  |  | 5 | 10 |
|  |  | 2.5 | 0 |
| 3V | Table 1 A No. 4 = B | 5 | 80 |
|  |  | 2.5 | 20 |

TABLE 4-continued

|  | Active ingredient or combination | Active ingredient concentration in the spray mixture in ppm | Efficacy in % of the untreated control |
|---|---|---|---|
| 4V | III a R = methyl pyrimethanil | 125 50 25 | 50 20 0 |
| 5V | III b R = 1-propynyl mepanipyrim | 125 50 25 | 0 0 0 |
| 6V | III c R = cyclopropyl cyprodinil | 50 | 85 |

TABLE 5

| Ex. | Active ingredient concentration in the spray mixture in ppm | Observed efficacy | Calculated efficacy*) |
|---|---|---|---|
| 7 | 12.5 A + 12.5 IIIa | 90 | 70 |
| 8 | 5 A + 50 IIIa | 80 | 28 |
| 9 | 2.5 A + 25 IIIa | 20 | 0 |
| 10 | 12.5 A + 125 IIIb | 97 | 40 |
| 11 | 5 A + 50 IIIb | 90 | 10 |
| 12 | 2.5 A + 25 IIIb | 30 | 0 |
| 13 | 5 A + 50 IIIc | 95 | 87 |
| 14 | 5 B + 50 IIIa | 80 | 68 |
| 15 | 5 B + 50 IIIb | 90 | 60 |
| 16 | 2.5 B + 50 IIIb | 80 | 20 |
| 17 | 5 B + 50 IIIc | 100 | 94 |

*)calculated using Colby's formula

The test results reveal that for all mixing ratios the observed efficacy exceeds the efficacy precalculated using Colby's formula.

EXAMPLES 18–34

Protective Activity Against *Puccinia recondita* on Wheat (Leaf Rust of Wheat)

Leaves of wheat seedlings cv. "Frühgold" in pots were sprayed to run-off with an aqueous spray mixture which had been prepared with a stock solution of 10% active ingredient, 63% cyclohexanone and 27% emulsifier. The next day, the leaves were moistened and dusted with leaf rust spores (*Puccinia recondita*). The pots were subsequently placed for 24 hours into a chamber with high atmospheric humidity (90 to 95%) at from 20 to 22° C. During this time, the spores germinated, and the germination tubes penetrated the plant tissue. The treated and infected plants were then grown in the greenhouse for a further 7 days at from 20 to 22° C. and a relative atmospheric humidity of 65 to 70%. The extent of rust development on the leaves was then determined visually.

The visually determined values for the percentage of infected leaf area were transformed into efficacy in percent of the untreated control. An efficacy of 0 is the same infection level as in the untreated control, an efficacy of 100 is an infection level of 0%. The expected efficacies for combinations of active ingredients were calculated using Colby's formula (Colby, S. R. (Calculating synergistic and antagonistic responses of herbicide Combinations", Weeds, 15, p. 20–22, 1967) and compared with the observed efficacies.

TABLE 6

| Ex. | Active ingredient or combinations | Active ingredient concentration in the spray mixture in ppm | Efficacy in % of the untreated control |
|---|---|---|---|
| 18V | Control (untreated) | (Infection level 100%) | 0 |
| 19V | Compound No. II.32 of Table 3 = C | 12.5 | 85 |
| | | 5 | 80 |
| | | 2.5 | 60 |
| | | 1.25 | 10 |
| 20V | Compound No. II.38 of Table 3 = D | 12.5 | 90 |
| | | 5 | 80 |
| | | 2.5 | 20 |
| 21V | IIIa R = methyl pyrimethanil | 125 | 50 |
| | | 50 | 20 |
| | | 25 | 0 |
| 22V | III b R = 1-propynyl mepanipyrim | 125 | 0 |
| | | 50 | 0 |
| | | 25 | 0 |
| | | 12.5 | 0 |
| 23V | IIIc R = cyclopropyl cyprodinil | 12.5 | 0 |

TABLE 7

| Ex. | Active ingredient concentration in the spray mixture in ppm | Observed efficacy | Calculated efficacy*) |
|---|---|---|---|
| 24 | 12.5 C + 125 IIIa | 97 | 93 |
| 25 | 5 C + 50 IIIa | 95 | 84 |
| 26 | 2.5 C + 25 IIIa | 95 | 60 |
| 27 | 5 C + 50 IIIb | 90 | 80 |
| 28 | 2.5 C + 25 IIIb | 85 | 60 |
| 29 | 1.25 C + 12.5 IIIb | 40 | 10 |
| 30 | 12.5 + 125 IIIa | 100 | 95 |
| 31 | 12.5 D + 125 IIIb | 100 | 90 |
| 32 | 5 D + 50 IIIb | 97 | 80 |
| 33 | 2.5 D + 25 IIIb | 80 | 20 |
| 34 | 2.5 D + 12,5 IIIb | 93 | 20 |
| 35 | 2.5 D + 12.5 IIIc | 70 | 20 |

*)calculated using Colby's formula

The examples of Examples 1–34 reveal that for all mixing ratios the observed efficacy exceeds the value precalculated using Colby's formula.

We claim:

1. A fungicidal composition comprising synergistically effective amounts of b) a carbamate of formula II (II)

wherein T is CH or N, n is 0, 1 or 2, R is halogen, $C_1$–$C_4$-alkyl or $C_1$–$C_4$-haloalkyl, and the radicals R are identical or different when n is 2, and c) a pyrimidine compound of formula III (III)

wherein R is methyl, propyn-1-yl or cyclopropyl.

2. The fungicidal composition defined in claim 1, comprising the carbamate and the compound of formula III in a weight ratio of from 20:1 to 0.1:2.

3. The fungicidal composition defined in claim 1, wherein T is CH, n is 1 and R is 4-Cl.

4. The fungicidal composition defined in claim 1, wherein R is methyl.

5. The fungicidal composition defined in claim 1, further comprising an oxime ether of formula I (I)

wherein

X is oxygen or NH;

Y is CH or N;

Z is oxygen, sulfur, NH or $C_1$–$C_4$-alkylamino; and

R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which is unsubstituted, partially or fully halogenated and/or carries from one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

6. The fungicidal composition defined in claim 5, comprising (i) the carbamate and/or the oxime ether and (ii) the compound of formula III in a weight ratio of from 20:1 to 0.1:2.

7. The fungicidal composition defined in claim 5, wherein T is CH, n is 1 and R is 4-Cl.

8. The fungicidal composition defined in claim 5, wherein R is methyl.

9. A method of controlling harmful fungi, which comprises treating the harmful fungi, their environment, or plants, seeds, soils, areas, materials or spaces which are to be kept free from said fungi with synergistically effective amounts of the carbamate and the compound of formula III defined in claim 1.

10. The method defined in claim 9, wherein the carbamate and the compound of formula III are applied simultaneously together or separately or in succession.

11. The method defined in claim 9, wherein the carbamate and the compound III are applied in a weight ratio of from 20:1 to 0.1:2.

12. The method defined in claim 9, wherein the carbamate is applied in an amount of from 0.01 to 0.5 kg/ha.

13. The method defined in claim 9, wherein the compound of formula III is applied in an amount of from 0.1 to 1.0 kg/ha.

14. The method defined in claim 9, wherein T is CH, n is 1 and R is 4-Cl.

15. The method defined in claim 9, wherein R is methyl.

16. A method of controlling harmful fungi, which comprises treating the harmful fungi, their environment, or plants, seeds, soils, areas, materials or spaces which are to be kept free from said fungi with synergistically effective amounts of the carbamate, the oxime ether and the compound of formula III defined in claim 5.

17. The method defined in claim 16, wherein the carbamate and the compound of formula III are applied simultaneously together or separately or in succession.

18. The method defined in claim 16, wherein (i) the carbamate and/or the oxime ether and (ii) the compound of formula III are applied in a weight ratio of from 20:1 to 0.1:2.

19. The method defined in claim 16, wherein the carbamate is applied in an amount of from 0.01 to 0.5 kg/ha.

20. The method defined in claim 16, wherein the oxime ether is applied in an amount of from 0.01 to 0.5 kg/ha.

21. The method defined in claim 16, wherein the compound of formula III is applied in an amount of from 0.1 to 1.0 kg/ha.

22. The method defined in claim 16, wherein T is CH, n is 1 and R is 4-Cl.

23. The method defined in claim 16, wherein R is methyl.

* * * * *